US009599570B2

(12) United States Patent
Quick

(10) Patent No.: US 9,599,570 B2
(45) Date of Patent: Mar. 21, 2017

(54) SYSTEMS AND METHODS TO MEASURE AND DISPLAY THE SCINTILLATION POTENTIAL OF A DIAMOND OR OTHER GEMSTONE

(71) Applicant: Jason Quick, Las Vegas, NV (US)

(72) Inventor: Jason Quick, Las Vegas, NV (US)

(73) Assignee: American Gem Society, Las Vegas, NV (US)

( * ) Notice: Subject to any disclaimer, the term of this patent is extended or adjusted under 35 U.S.C. 154(b) by 593 days.

(21) Appl. No.: 14/051,215

(22) Filed: Oct. 10, 2013

(65) Prior Publication Data

US 2014/0097354 A1   Apr. 10, 2014

Related U.S. Application Data

(60) Provisional application No. 61/712,126, filed on Oct. 10, 2012.

(51) Int. Cl.
*G01N 21/87*   (2006.01)
*G01N 21/64*   (2006.01)

(52) U.S. Cl.
CPC ............ *G01N 21/87* (2013.01); *G01N 21/64* (2013.01)

(58) Field of Classification Search
CPC ...................................................... G01N 21/87
USPC ............................................................ 702/35
See application file for complete search history.

(56) References Cited

U.S. PATENT DOCUMENTS

2007/0222972 A1\* 9/2007 Sasian .................... G01N 21/87
356/30
2009/0153835 A1\* 6/2009 Sasian .................... G01N 21/87
356/30

\* cited by examiner

*Primary Examiner* — Bryan Bui
(74) *Attorney, Agent, or Firm* — Lewis Rice LLC

(57) ABSTRACT

Systems and methods for generating an image of a gemstone under evaluation which is coded according to angular ranges in its angular spectrum across a broad range of tilts, this allows for scintillation of a gemstone to be demonstrated based on a singular coded image of the gemstone. Scintillation information is thus presented in a single image, or as a plurality of images showing fire scintillation, flash scintillation, and other scintillation related criteria as a series of static images.

10 Claims, 9 Drawing Sheets

SYSTEMS AND METHODS TO MEASURE AND DISPLAY THE SCINTILLATION POTENTIAL OF A DIAMOND OR OTHER GEMSTONE

CROSS REFERENCE TO RELATED APPLICATION(S)

This application claims the benefit of U.S. Provisional Patent Application Ser. No. 61/712,126, filed Oct. 10, 2012, the entire disclosure of which is herein incorporated by reference.

BACKGROUND OF THE INVENTION

1. Field of the Invention

This disclosure is related to the field of diamond and gemstone grading. Specifically to systems and methods for evaluating the scintillation of a diamond and presenting that evaluation in a static comparative format.

2. Description of Related Art

Diamonds have traditionally been graded based on what is known as the four C's: color, clarity, carat weight, and cut. Other than carat weight which is directed to the actual size of the stone, the other three factors attempt to quantify or rank diamonds which are objectively better than others. The parameters, therefore, are ways of indicating how light interacts with the diamond, whether the stone appears bright and lively, and whether the diamond appears to produce color or not.

While the four C's have a long standing tradition, they are, in many respects, a stand in for what is a subjective appearance to a user. Instead of talking about more objective grading standards, many users instead will focus on what they see in a diamond. This may relate to color or to "liveliness" of a diamond. A well cut diamond, when moved, will often appear to include many different colors of light in a number of different locations making the stone have what appears to be a large amount of internal movement, color, and prismatic effect.

Generally, a diamond's effect on light is characterized by referring to the stone having fire, brilliance, or scintillation. All of these terms relate to the stone's ability to reflect, refract, or otherwise act on incoming light in a particular fashion. Brilliance is generally the stone's ability to redirect white light toward a viewer, scintillation is generally the apparent movement or flashing of light in the stone, and fire is generally the ability of the stone to disperse light and produce colors which appear to be within the stone. Scintillation is often colloquially referred to as "sparkle" since the flashing points of light make the gemstone appear to sparkle as it is moved.

Interestingly, cutting a diamond for one effect will often lower the ability to see other effects. For instance, a very brilliant diamond will often appear to not have much fire or scintillation. While color or movement may be being produced under certain conditions, the color and changes may be washed out by the high level of white light. Therefore, it often requires examination of a stone under many different lighting conditions to see its true attributes.

Because of the complexity of a diamond's geometry as well as the different kinds of environments in which it may be viewed, purchasing diamonds is often very frustrating for a consumer. They may look at a diamond and think it is attractive, but are concerned that what they like is not objectively "better" or that they are being overcharged for an item which is as much an investment as a purchase. For this reason, an ability to objectively evaluate and also to more systematically explain and display the properties of a particular diamond are desirable.

As the effect of scintillation is flashes of white or colored light that appear when the gemstone, the observer, or the illumination is in movement, it can often be difficult to demonstrate or quantify the scintillation of a diamond. The effect of scintillation is sometimes demonstrated to a potential purchaser by moving a gemstone under a given illumination scenario. This can provide the ability to compare the scintillation of multiple diamonds provided at a single time, but often does not allow for comparison of diamonds which are separated by physical or temporal space. Further, since the effect can be specific to lighting conditions, it often requires that the presentation be made in a live setting, which can be difficult in certain retail environments.

Further, in the jewelry industry there is generally a need to evaluate the illumination effects of brilliance, fire, and scintillation for gemstone grading purposes so that a purchaser of a diamond or other gemstone has a generally objective measure of the quality of the gemstone. This grade then needs to be provided as part of a grading document which can be provided with the gemstone to a consumer. Grading allows the user to better quantify the "value" of the diamond for purposes such as insurance, investment, and potential replacement, and also helps to create and regulate the market for gemstones by providing universal objective criteria which can be used in pricing and comparison. While a diamond grade does not necessarily reflect subjective "beauty" of a gemstone and many gemstones of low grade are undeniably beautiful, a diamond grade can be used to effect price and value comparisons that can assist with comparisons between diamonds by creating a market with objective external criteria.

The use of objective criteria to evaluate the light performance of a diamond is well known. U.S. Pat. Nos. 6,665,058; 6,795,171; 7,336,347; 7,372,552; 7,382,445; 7,355,683; 7,420,657; 7,580,118; and 7,751,034, the entire disclosure of all of which is herein incorporated by reference, all discuss methodologies and presentation methods by which various light handling properties of gemstones can be objectively evaluated and presented to a customer, retailer, or investor. However, while these methods and systems are very valuable, they primarily focus on the static (that is non-movement related) light handling properties of the gemstone such as fire and brilliance.

Scintillation has been notoriously hard to quantify in any type of fixed grading criteria because it is inherently a dynamic effect and requires relative movement. There are generally two types of scintillation, flash scintillation and fire scintillation. These are discussed in, for example, "Evaluation of Brilliance, Fire, and Scintillation in Round Brilliant Gemstones," Optical Engineering (2007), the entire disclosure of which is herein incorporated by reference. That work defines and characterizes gemstone scintillation as follows: "In the presence of brilliance and fire the most appealing effect is gem scintillation. In this effect the fire pattern changes dynamically and flashes of white light are perceived across the crown of the stone. Thus, there are two major scintillation effects, fire and flash scintillation. To observe them it is required that the stone, the observer, or the illumination conditions be in movement."

Because scintillation is a dynamic effect, the effect of scintillation is sometimes demonstrated by moving a gemstone under a given illumination scenario, or by computer simulation of the same. Such systems and methods are discussed in, for example, U.S. Pat. No. 8,098,369, the entire disclosure of which is herein incorporated by reference. While such systems and methods can be very useful when computational machines are available, or in live presentations, it can be difficult to provide such a scintillation evaluation in a form that is readily useable for insurance evaluation, or other record keeping on the gemstone. Typically, grading information needs to be placed on a paper document that can be provided with the gemstone to the retailer and then end consumer by a grading lab or other outside authority. Scintillation methods have generally, at best, required computer storage media with the evaluation thereon to be provided to the end consumer, and this can be undesirable for certain types of grading documents.

SUMMARY OF THE INVENTION

Described herein, among other things, is a method, system and device (generally a specifically programmed computer processor) to evaluate the scintillation effects of gemstones for the purpose of gemstone grading. The methodology is independent of illumination scenario and is based on the so-called angular spectrum of a gemstone. The angular spectrum provides the critical illumination directions that can make the facets (or virtual facets, which are those produced as light is partitioned by actual cut facets) of a stone appear illuminated when it is observed from a given point in relation to the gemstone. This point is typically between 20 cm and 60 cm above the gemstone crown and represents a likely point of observation for most jewelry.

In addition, in these methods an image of a gemstone under evaluation is color-coded (alternatively figure, shade, or symbol-coded) according to angular ranges in its angular spectrum across a broad range of tilts. This allows for scintillation of a gemstone to be demonstrated based on a singular coded (color, figure, shade, symbol, etc.) image of the gemstone. Thus, scintillation information may be presented in a single image, or as a plurality of images showing fire scintillation, flash scintillation, and other scintillation related criteria as a series of static images. These images can be reproduced as part of a paper grading document or as any other form of simplified display.

There is described herein, among other things, a method to display the scintillation of a gemstone, the method comprising: acquiring the angular spectrum of an oriented gemstone relative a point of observation by: tracing a ray to said gemstone from said point of observation to a point of intersection of said gemstone; propagating said ray in said gemstone until it exits said gemstone; determining a region of a hemisphere arranged about said gemstone that said ray intersects; coding said point of intersection with a value according to said region that said ray intersects; repeating said steps of tracing, propagating, determining and coding for a plurality of points of intersection of said gemstone; tilting said gemstone to a new orientation relative to said point of observation and repeating said acquiring for said gemstone in said new orientation relative to said point of observation; repeating said tilting a pre-determined number of times; averaging said values for each point of intersection from all said acquiring; and mapping said average value of an associated point of intersection to said associated point of intersection on an image of said gemstone.

In an embodiment of the method, said gemstone is a diamond.

In an embodiment of the method, said rays correspond to white light and said mapping displays flash scintillation potential.

In an embodiment of the method, said rays correspond to colored light and said mapping displays fire scintillation potential.

In an embodiment of the method, said mapping includes virtual facets.

In an embodiment of the method, said mapping comprises color-coding.

In an embodiment of the method, said mapping comprises shading.

There is also described herein a scintillation potential map produced by any of the methods described above.

There is also described herein a computer system for evaluating a gemstone, the system comprising: means for acquiring the angular spectrum of an oriented gemstone relative a point of observation by: tracing a ray to a computer readable representation of said gemstone from said point of observation to a point of intersection of said gemstone; propagating said ray in said gemstone until it exits said gemstone; determining a region of a hemisphere arranged about said gemstone that said ray intersects; coding said point of intersection with a value according to said region that said ray intersects; and repeating said steps of tracing, propagating, determining and coding for a plurality of points of intersection of said gemstone; means for tilting said computer readable representation of said gemstone to a new orientation relative to said point of observation and repeating said acquiring for said computer readable representation of said gemstone in said new orientation relative to said point of observation; means for repeating said tilting a pre-determined number of times; means for averaging said values for each point of intersection from all said acquiring; and means for mapping said average value of an associated point of intersection to said associated point of intersection on an image of said gemstone.

There is also described herein a non-transitory computer readable medium comprising: computer readable instructions for acquiring the angular spectrum of an oriented gemstone relative a point of observation by: tracing a ray to a computer readable representation of said gemstone from said point of observation to a point of intersection of said gemstone; propagating said ray in said gemstone until it exits said gemstone; determining a region of a hemisphere arranged about said gemstone that said ray intersects; coding said point of intersection with a value according to said region that said ray intersects; and repeating said steps of tracing, propagating, determining and coding for a plurality of points of intersection of said gemstone; computer readable instructions for tilting said computer readable representation of said gemstone to a new orientation relative to said point of observation and repeating said acquiring for said computer readable representation of said gemstone in said new orientation relative to said point of observation; computer readable instructions for repeating said tilting a pre-determined number of times; computer readable instructions for averaging said values for each point of intersection from all said acquiring; and computer readable instructions for mapping said average value of an associated point of intersection to said associated point of intersection on an image of said gemstone.

While presented in black and white (greyscale) these figures could be provided in color by substituting specific colors for the various shades.

Figures 1A, 1B, 1C:
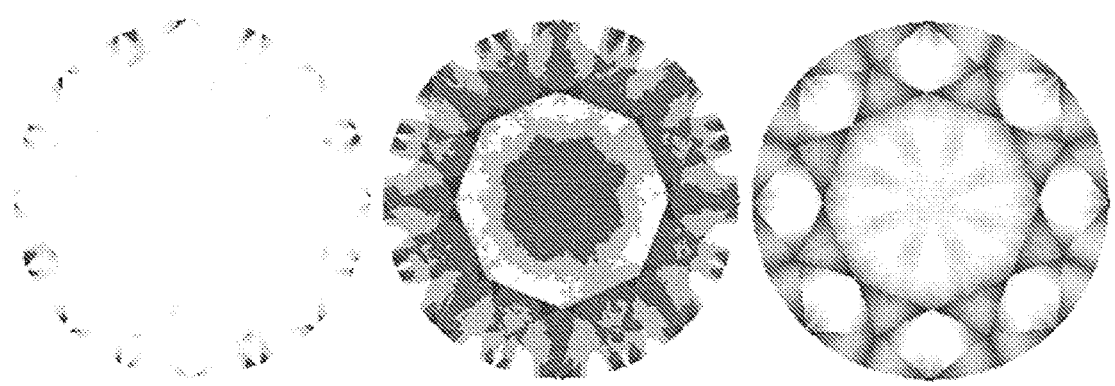
FIG. 1A provides an embodiment of a flash scintillation map, FIG. 1B a fire scintillation map, and FIG. 1C a virtual facet patterning map for a well cut round brilliant diamond.
Figure 2A:
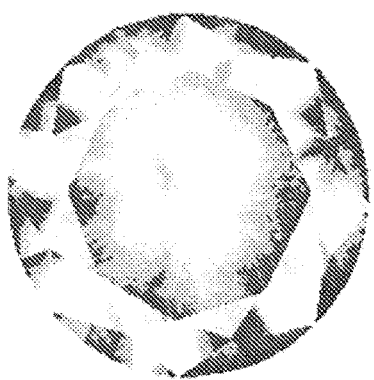
Figure 2B:
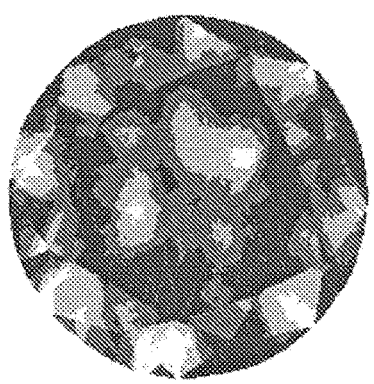
Figure 2C:
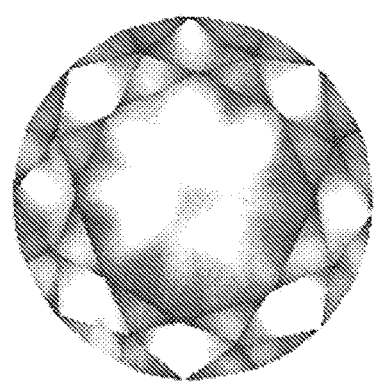

FIG. 2A provides an embodiment of a flash scintillation map, FIG. 2B a fire scintillation map, and FIG. 2C a virtual facet patterning map for a round brilliant diamond that is not cut as well as that of the corresponding FIGS. 1A-1C. While presented in black and white (greyscale) these figures could be provided in color by substituting specific colors for the various shades.

Figure 3:
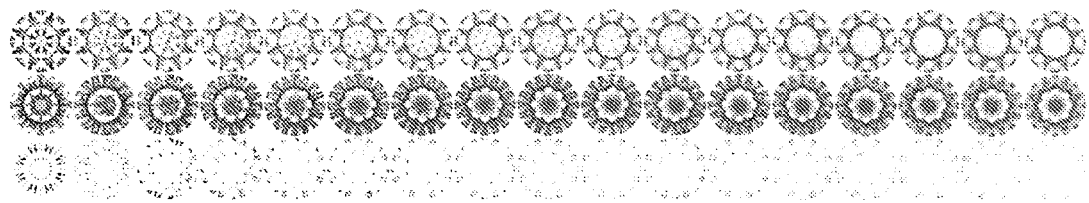

FIG. 3 provides an embodiment of a series of flash scintillation maps (bottom row), fire scintillation maps (middle row), and virtual facet patterning maps (top row). The series shows how cumulative tests are used to provide for a gradually more comprehensive map as the columns progress from left to right.

Figures 4A, 4B, 4C, 4D, 4E, 4F, 4G:
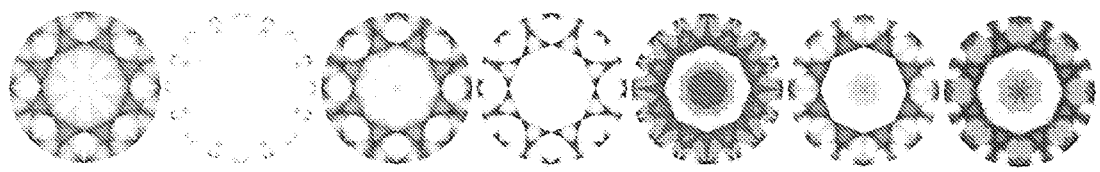

FIGS. 4A-4G provide various image maps. Specifically, FIG. 4A provides a virtual facet (VF) size map, FIG. 4B a flash scintillation map, and FIG. 4C a first VF weighted flash map based on the VF size map of FIG. 4A and flash scintillation map of FIG. 4B. FIG. 4D provides a second VF weighted flash map based on the VF size map of FIG. 4A and flash scintillation map of FIG. 4B. FIG. 4E provides a fire scintillation map. FIG. 4F provides a first VF weighted fire scintillation map based on the VF size map of FIG. 4A and the fire scintillation map of FIG. 4E, and FIG. 4G provides a second VF weighted fire scintillation map based on the VF size map of FIG. 4A and fire scintillation map of FIG. 4E.

Figure 5:
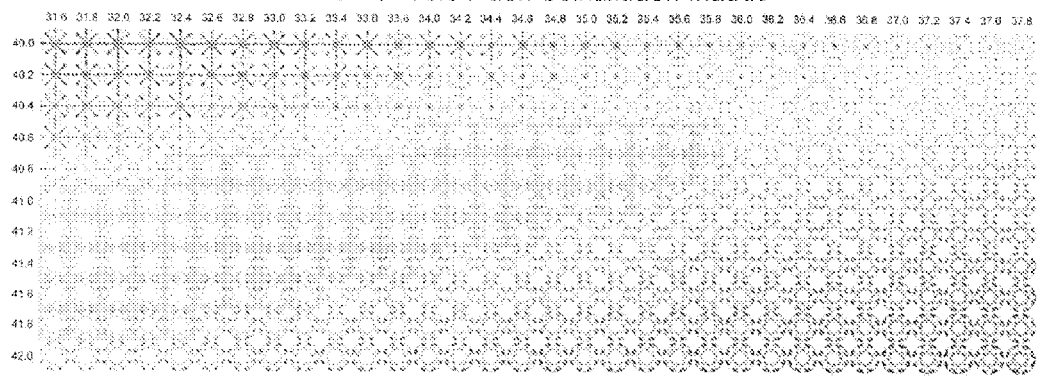

FIG. 5 provides an embodiment of a flash scintillation matrix for 57% table.

Figure 6:
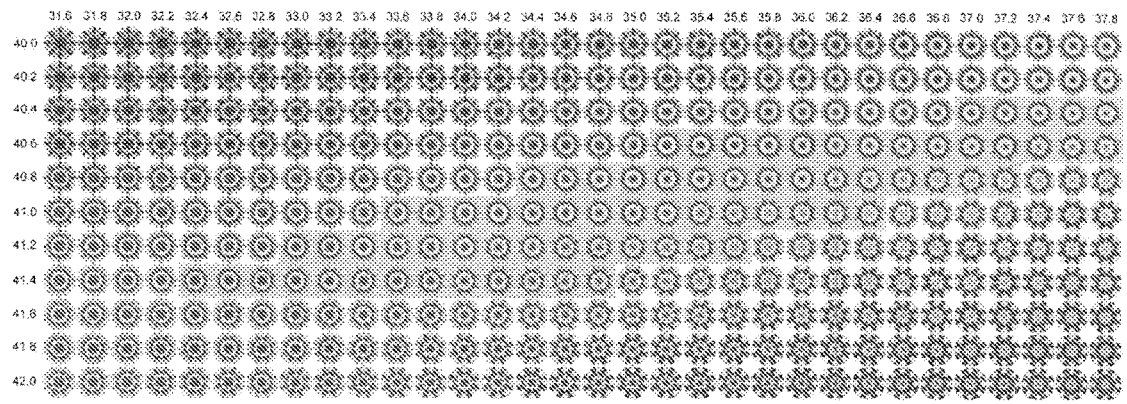

FIG. 6 provides an embodiment of a fire scintillation matrix for 57% table.

Figure 7:
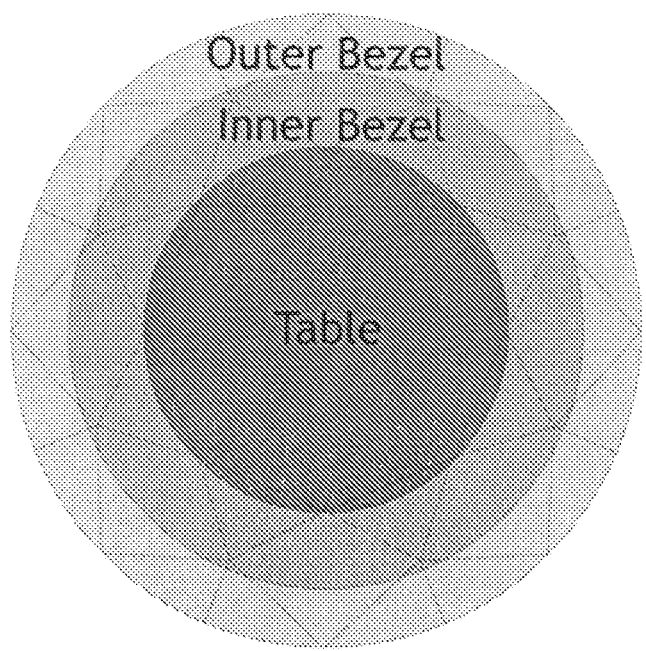

FIG. 7 provides an embodiment of three concentric zones which can be used for scintillation assessment in an embodiment of the invention.

Figure 8:
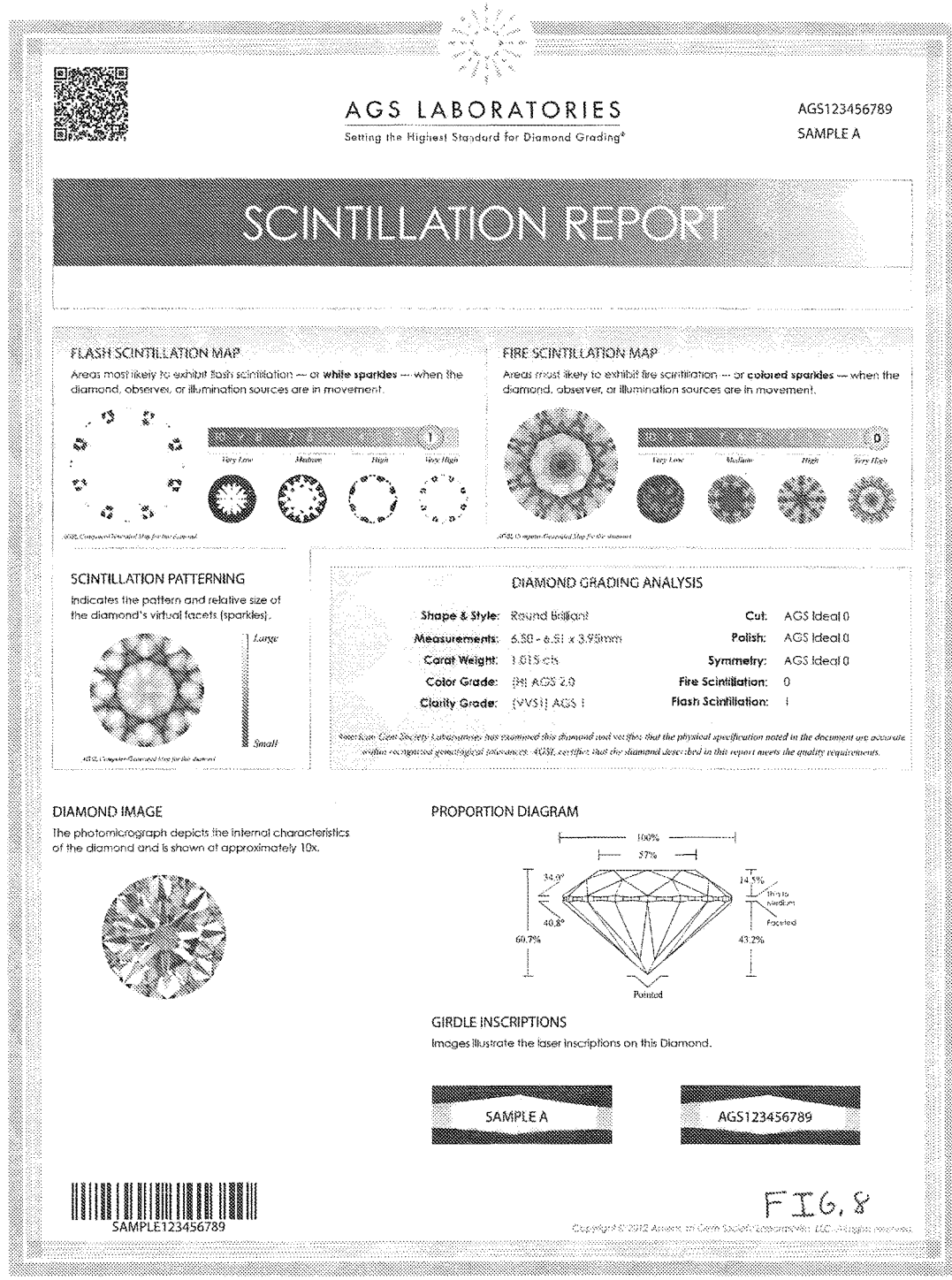

FIG. 8 provides an embodiment of a diamond grading report for a well cut diamond utilizing scintillation maps.

Figure 9:
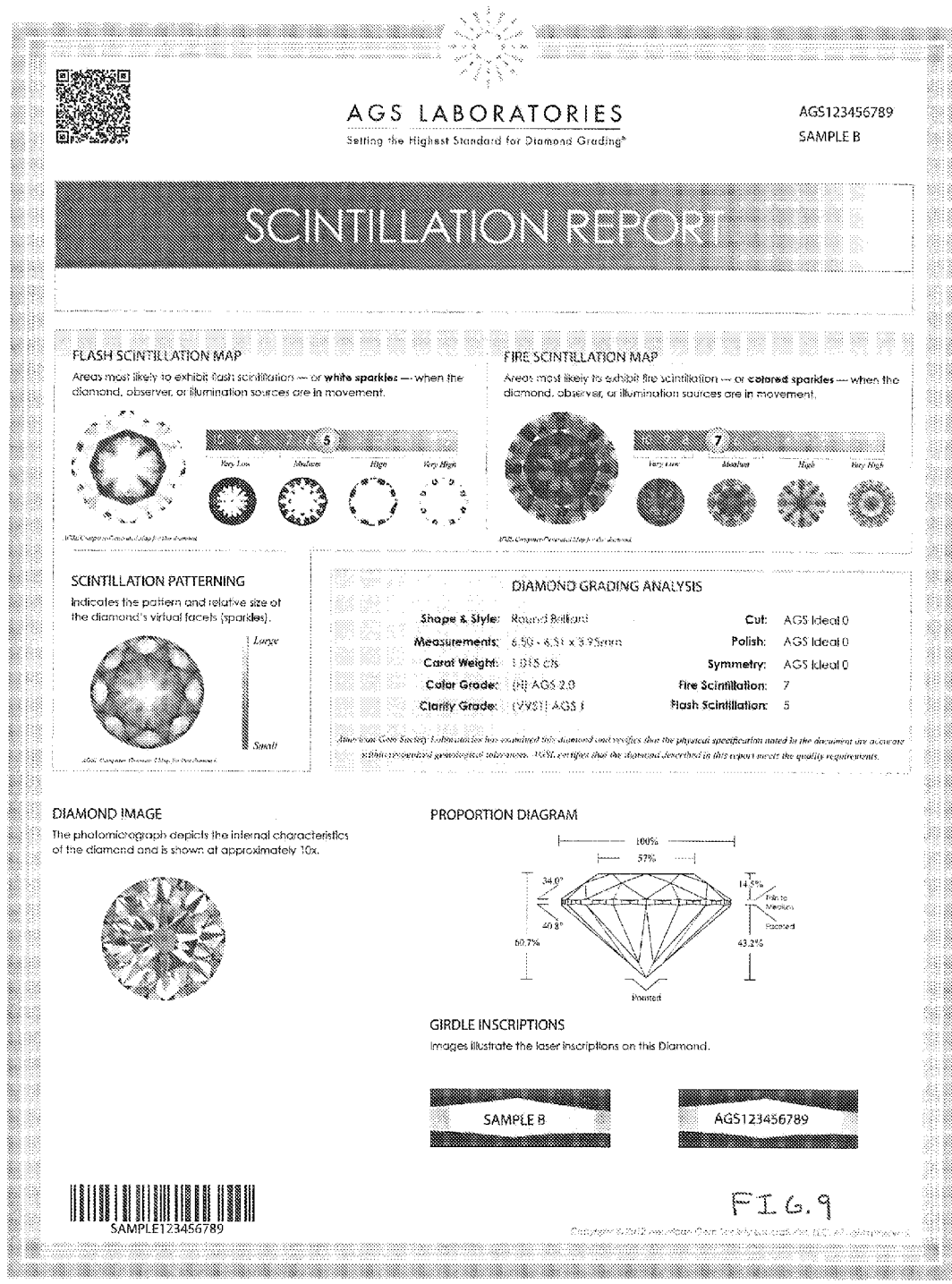

FIG. 9 provides an embodiment of a diamond grading report for a diamond that is not cut as well as the diamond of FIG. 8 utilizing scintillation maps.

DESCRIPTION OF THE PREFERRED EMBODIMENT(S)

A primary challenge with evaluating and representing scintillation is that it is a dynamic phenomenon requiring that something be in motion whether that is the observer, the diamond, or the light sources. Sparkles are turning on and off, so the sparkle patterning of the gemstone, usually a diamond, is changing as a function of time. Due to this dependence of movement and change, videos and computer animations have traditionally been the natural ways to display scintillation. However, for the purposes of gemstone evaluation, it is useful to display the scintillation potential of the stone as a static image so that it can be provided on a paper report or similar static display.

The scintillation maps and grading system disclosed herein can provide for improvement in the understanding, representation, and assessment of scintillation. The scintillation maps compress the dynamic information of a video or animation into a single static image. This enables the scintillation potential of the stone to be captured in a static image which has many uses in the jewelry industry, including the representation of scintillation potential on a report, the comparison of the scintillation potential of different stones, the objective ranking (e.g. by numerical scale) of the scintillation potential of different stones, the ability to improve gemstone cutting to maximize scintillation (including the development of new designs and patterns of cut), and the assessment of gemstone scintillation.

Behind the scintillation potential maps is the idea of a cumulative map. A cumulative map can be thought of as a collection of static color-coded maps "sandwiched" together and averaged into a single map. Rather than averaging the individual values of the pixels, it is the underlying data points corresponding to the pixels which are averaged and then converted into the color coded "cumulative map".

Cumulative maps are utilized in this method to "average" the data collected over a series of orientations into a single cumulative coded map. A 3-D model of the diamond is ray traced over a series of orientations (tilts) to create an array of data and a series of coded maps corresponding to each orientation of the diamond. Each of the individual maps represent a "snapshot" of data correlating to relevant scintillation factors such as virtual facet size, flash potential, and dispersion. The individual maps are then "sandwiched" into a single static map, by averaging the underlying data used to create the maps. The results of the averaging are static coded maps representing different aspects or characteristic of scintillation.

While an individual snapshot is inadequate for determining the scintillation potential of a moving stone, the cumulative effect of each of the "snapshots" contribute to the overall scintillation characteristics of a moving gemstone. Broadly speaking, gemstones that can reflect light from a source to a user and thereby appear bright across a broad range of tilts (orientations) are more likely to exhibit flash scintillation than stones that cannot. Likewise, the fire scintillation potential of a moving diamond is also highly dependent on the fire potential of static orientations (the ability to reflect portions of the light in different directions or refract the light) comprising the "snapshots" of the moving diamond. For these reasons, the cumulative flash and fire scintillation maps are useful for assessing and displaying important characteristics related to the scintillation of a diamond. Further, cumulative maps can quickly display non-symmetrical variations in a diamond cut.

U.S. Pat. Nos. 6,665,058; 6,795,171; 7,336,347; 7,372,552; 7,382,445; 7,355,683; 7,420,657; 7,580,118; 7,751,034; and 8,098,369, the entire disclosures of which are herein incorporated by reference, provide for various embodiments of evaluation methodologies that can be used to determine the light handling characteristics (or ability to produce scintillation when certain conditions are met) of a diamond or other gemstone in any orientation. The methods and systems discussed therein can be used to evaluate the light handling properties of a diamond or other gemstone for purposes of the presentation discussed herein and the generation of a cumulative map, or other methods and systems may be used in alternative embodiments.

FIG. 1A provides an image referred to as a flash potential map. The white areas in the map correspond to areas where sparkles (light flashes—the effect of scintillation) are most likely to be seen when the diamond is in motion, while the dark areas correspond to areas where light is least likely to be seen. Likewise, the fire scintillation map in FIG. 1B, is shaped according to where fire scintillation (color flashes) are most likely to be observed. In an alternative embodiment, to better represent "fire" and clarify the difference of display from FIGS. 1A and 1B, the shading of FIG. 1B is replaced by a red spectrum color coding (e.g. using yellow, orange, and red instead of white, grey, and black). FIG. 1C is coded according to expected sparkle size based on virtual facets. The lighter areas represent the areas where the largest sparkles should be observed when the diamond is motion, and the darkest areas correspond to smaller or no sparkles. FIG. 1C shows the virtual facets, or, in effect, the individual "mirror" surfaces that the user would see sparkling. The images in FIGS. 1A-IC, were created by virtually tilting the gemstone under evaluation through 81 different orientations and averaging the results of each evaluation, at each point of the visible area, in a single cumulative map.

The images in FIGS. 2A-2C represent the same three maps as FIGS. 1A-1C, but for a different stone. The stone in FIGS. 2A-2C was purposefully chosen due to lack of symmetry and what would generally be considered poor light handling characteristics. A comparison of the scintillation maps of the two stones suggests the stones would exhibit clearly different scintillation characteristics and illustrate how the maps can be used comparatively. In particular, the large dark areas in the flash scintillation map of FIG. 2A, suggests that sparkles would be less likely to be observed in these areas relative to the gemstone corresponding to the map in FIG. 1A. Furthermore the stone would be less likely to exhibit fire scintillation (FIG. 2B) as illustrated by the increased amount of dark area. Finally, the gemstone has a very different distribution of virtual facet (sparkle) sizes (FIG. 2C) when the stone was observed in motion and the virtual facets are not as well defined. As should also be apparent, the patterns of FIGS. 2A-2C are clearly less symmetrical than those of FIGS. 1A-1C indicating that the stone's orientation can potentially hinder scintillation potential.

An embodiment of an "averaging" method to produce cumulative maps which was used to generate FIGS. 1A-2C is illustrated in FIG. 3. The rows correspond to the three types of maps of FIGS. 1A-2C. The top row of FIG. 3 corresponds to the virtual facet size maps of FIGS. 1C and 2C, the middle row corresponds to the fire scintillation potential map of FIGS. 1B and 2B and the lower row corresponds to the flash scintillation potential map of FIGS. 1A and 2A. Each column corresponds to the resultant map based on the number of orientations measured, where the images in nth column correspond the cumulative maps generated based on the cumulative n orientations. In FIG. 3 there are 17 total different orientations where the light performance is measured, and the values are combined together. This is a relatively small number compared to the generation of the maps of FIGS. 1A-2C where 81 orientations were used.

Column one of FIG. 3 provides only a single orientation. In this embodiment, the face-up orientation (looking directly down perpendicular to the gemstone's table) is used. Column two provides for the cumulative average of the first two orientations which would generally comprise the face-up orientation of column one, and an orientation with the stone tilted from perpendicular in a selected direction. The exact amount of tilt will be determined by the number of different tests being performed (n) and by the desired total tilt they will be through. This will continue so that for any column n the map is the cumulative average of all orientations 1 through n.

Depending on embodiment, the number and choice of columns can vary. For example, in one embodiment, the first n/4 columns may correspond to rotations of the gemstone in a first direction, the next n/4 columns may correspond to rotations of the gemstone in the opposite direction (180 degrees different), the next n/4 columns may correspond to a right tilt (90 degrees different), and the final n/4 columns may correspond to a left tilt (270 degrees different). Alternatively or additionally, the gemstone may be tilted a complete 360 degrees in an initial direction (rotated entirely around), or any subset thereof. It should be recognized that the specific rotations of the gemstone are not as important as the fact that the stone has been rotated through a number of different tilts relative to the defined observation point.

In some embodiments, ray tracing techniques are employed to determine the value for any point P and selected orientation. This will generally be performed utilizing a computer model of the gemstone to be analyzed and ray tracing software running on a computer processor. First the orientation of the gemstone is initially selected. This is generally initially the position where the table is perpendicular to an observation point above the center of the table. For each point P on the crown of the diamond, the path travelled when the ray travels from the point P and through the stone characterizes and defines which virtual facet point P belongs to. For example, a possible ray path in a reverse ray trace for a standard round brilliant gemstone may be: start at a hypothetical eye (observer) above the table and travel to a Point P on the table. At this point there is an air to gem material refraction. The ray trace may then travel to the pavilion main 1 in its first reflection, from there to the pavilion main 5 in its second reflection, and out to the crown main 5 where it exists the gemstone and has another gem material to air refraction. The ray will then travel linearly and intersect a hemisphere of radius R about the gemstone at a coordinate (x,y,z). An embodiment of a ray tracing technique such as this is discussed in U.S. Pat. No. 7,336, 347, the entire disclosure of which is herein incorporated by reference. The coordinate x,y,z defines the point where a source of incoming light would cause a reflection that is visible to the originally defined observer.

Depending on the relative location of x,y,z compared to likely light sources (e.g. light is generally strongest around the head of the observer) the point P can be provided with a value of how much light is sent to the observer based on the location of x,y,z (e.g. within a certain area band). This process is repeated for a large number of points on the gemstones upper area, to get a value for all of them. The gemstone is then tilted relative to the observer, and the process is repeated. This is repeated for all tilts, and then the collection of values for all points P are averaged to provide for a flash scintillation map such as that of FIGS. 1A and 2A.

To produce a fire scintillation map such as that of FIGS. 2B and 2C the process is generally similar. However, in this calculation, the ray will often comprise two rays of different wavelength and the coordinate x,y,z will instead be two coordinates. If these are sufficiently far apart, the point is considered to have produced a visible color effect. The point can then be classified with a value based on one or both of the location of the relative coordinates and their relative distance from each other.

In order to facilitate computation, in an embodiment the ray tracing is performed where the ray paths and virtual facet patterns are "memorized" for each orientation of the stone in order to facilitate and accelerate computation. For sufficiently small orientation differences (tilt or relative location of P) the rays travelling through multiple points P or multiple tilts on the gemstone will travel through the exact same path through the 3-D model (e.g. the pathway described above will not change). Such a lack of change across multiple points P will, therefore, result in the rays being considered as interacting with the same virtual facet as such lack of change would produce a consistent light appearance (the points would behave the same). The direction vector of the exiting ray will likely change slightly (the x,y,z coordinates of impact on the hemisphere will be slightly different), but because P is still part of the same virtual facet, the intersection point on the hemisphere will be close to the other nearby orientations.

Said differently, P smoothly "scans" the panorama as the stone is moved, but will "jump" to a different area of the panorama when the ray paths corresponding to P changes (when one of the steps, e.g. reflection number two is no longer present) and therefore the virtual facet associated with P changes. This essentially provides the edge of the facet as this would be a break observed by the user. This observation (and similar observations for lack of change in the same point as the tilt changes) can yield an improved algorithm for determining cumulative maps and for creating the "dynamic scintillation" maps discussed later in this disclosure as it allows for significantly reduced computer processing.

In effect, this method allows for the light performance to be defined not by its relative value, as is common in fire and brilliance maps, but by the edge and point of transition. As a transition will likely correspond to a perceptible sparkle (and on/off or off/on transition) or the edge of a virtual facet this can provide for valuable information about the frequency and size of scintillation events.

By "memorizing" the ray paths associated with each point P and each orientation o, it is possible to determine the ray paths associated with some P for some orientations, without actually ray tracing the stone. For the points P on the crown of the stone, where the ray paths and virtual facets are identical between adjacent orientations, rays traced through P will also travel the same path through the 3-D model and result in the same VF for all orientations between the two adjacent orientations. To put this another way, it can be possible to eliminate the measurements between certain points because all the results for values between those points are the same.

This technique yields two primary benefits. Specifically, there is firstly speed-up in ray tracing time, as the technique enables the skipping of some ray tracing and/or incorporates "intelligent" guessing of the ray paths for different orientations. Secondly, an absolute cumulative map can be produced, generated by an averaging over "all" possible orientations within a certain range of possible orientation even though only selected points and orientations were actually computed. While employing successively higher numbers of discrete orientations in the cumulative map modeling, of say 25, 81, or 8001 orientations, converges quickly to what is effectively an absolute map, the technique described above is useful for computing the maps and datasets corresponding to the absolute limit of the process with a reduced number of computations being performed.

In addition to generating useful maps to represent and display the scintillation potential of gemstones, the methods utilized to generate the various maps are also useful for grading via a single letter, number, or other comparative grade the scintillation of a gemstone. A key attribute shared by the most scintillating diamonds is that they sparkle across the full crown of the stone. Weaker cuts frequently have non-productive areas (points or areas where no scintillation occurs) either in the table and/or the outer edges of the stone. In these non-productive areas no or few sparkles are generally seen regardless of orientation. This can be due to the area being particularly small, only reflecting light from sources which are likely to be relatively weak, or having few changes in source light orientation. This is one of the values of displaying the scintillation potential in terms of flash and fire scintillation maps as shown in FIGS. 1A-2C. The non-productive areas of the stone are immediately evident in the maps (the black areas) which visually supports assessment methodologies based on measuring the scintillation potential across different zones of the diamond such as is shown in FIG. 7.

While the scintillation potential maps of FIGS. 1A-2C can be used to compare the scintillation characteristics of two different diamond designs (cuts), the maps are especially useful for discriminating between the flash and fire scintillation potential between different gemstones cut to the same facet arrangement. A useful technique for establishing the "thresholds" for such discrimination is to create matrices of flash, fire and dynamic scintillation maps across a broad range of proportion sets. For example, FIGS. 5 and 6 represent the flash and fire scintillation matrices respectively for a standard round brilliant with a 57% table. The crown angles (horizontal axis) range from 31.6 to 37.8 degrees in 0.2 degree increments and the pavilion angles (vertical axis) range from 40.0 to 42.0 in 0.2 degree increments. Thus, these tables show a large number of proposed gemstone shapes with certain similar dimensions, and other dimensions changing. The proportions yielding the best fire and flash scintillation available generally lie near the diagonal from the bottom left corner to the top right corner and are shaded in both matrices. On the other hand, the maps illustrating the weakest flash and fire potential maps are those in the top left corner and bottom right hand corner of the matrices. These portions of the maps correspond to proportion sets that would receive lower flash/fire scintillation grades due to lower average flash and fire scintillation scores. As these happen to be on essentially parallel diagonals, grading values may be assigned based on relative diagonal position for a stone of particular dimensions. However, one can see that there are certain specific ratios of proportion that provide both high flash and fire potential.

When the diamond is ray traced, data sets are collected for every orientation that are then averaged into cumulative maps and data sets. These maps and data sets can then be analyzed and assessed to grade (for example provide a numerical rating which can be compared across stones) the stone or can be provided "as is" as part of an illustration of particular features of a stone as is shown in the grading documents of FIGS. 8 and 9.

In one embodiment to produce an objective "score" for the diamond, the cumulative flash map is divided into three concentric "zones" (for example, as indicated in FIG. 7) of equal area and the average flash values for each region is used to compute flash scintillation deductions. In turn, the average flash values in each of the zones can be assessed according to the "Average" flash or fire scores of all points within the zone and also according to the areas of the highest and/or lowest flash potential areas (e.g. a standard deviation). Such an assessment leads to a summary dataset containing dozens of values which can be used to grade the stone. One of the methods used to grade the stone, is to compare each entry of the summary dataset with a threshold to determine if a grading deduction for the specific category (i.e. table region, average flash value) should be applied to a default grade. The thresholds used can be determined from analyzing the matrices as described above in FIGS. 5 and 6. In other methods, both the standard flash, fire, and dynamic scintillation maps and the VF weighted versions of these maps are used to grade the scintillation potential of the scale. This yields even more data fields which can be used to determine the grade.

While the manners in which grades can be assigned is essentially endless, below is a list of twenty-four possible summary dataset values that can be used in one embodiment of assessing flash scintillation potential. Each of these values would generally be generated for a particular gemstone and compared with a standardized threshold in order to determine deductions. Similar data values can be used to assess fire scintillation potential and dynamic scintillation potential. The listing is arranged with each threshold having three indicators of its value. The first is the type of scintillation potential being evaluated (e.g. weighted or unweighted by virtual facets, FIGS. 4A-4G), the second provides the specific area of the gemstone being considered (FIG. 7), and the third provides the numerical value computed for the region.
(1) Standard Flash map-Total Crown-Average Flash.
(2) Standard Flash map-Table Region-Average Flash.
(3) Standard Flash map-Inner Bezel Region-Average Flash.
(4) Standard Flash map-Outer Bezel Region-Average Flash.
(5) Standard Flash map-Total Crown-Normalized area corresponding to high flash potential.
(6) Standard Flash map-Table Region-Normalized area corresponding to high flash potential.
(7) Standard Flash map-Inner Bezel Region-Normalized area corresponding to high flash potential.
(8) Standard Flash map-Outer Bezel Region-Normalized area corresponding to high flash potential.
(9) Standard Flash map-Total Crown-Normalized area corresponding to low flash potential.
(10) Standard Flash map-Table Region-Normalized area corresponding to low flash potential.
(11) Standard Flash map-Inner Bezel Region-Normalized area corresponding to low flash potential.
(12) Standard Flash map-Outer Bezel Region-Normalized area corresponding to low flash potential.
(13) VF weighted Flash map-Total Crown-Average Flash.
(14) VF weighted Flash map-Table Region-Average Flash.
(15) VF weighted Flash map-Inner Bezel Region-Average Flash.
(16) VF weighted Flash map-Outer Bezel Region-Average Flash.
(17) VF weighted Flash map-Total Crown-Normalized area corresponding to high flash potential.
(18) VF weighted Flash map-Table Region-Normalized area corresponding to high flash potential.
(19) VF weighted Flash map-Iamer Bezel Region-Normalized area corresponding to high flash potential.
(20) VF weighted Flash map-Outer Bezel Region-Normalized area corresponding to high flash potential.
(21) VF weighted Flash map-Total Crown-Normalized area corresponding to low flash potential.
(22) VF weighted Flash map-Table Region-Normalized area corresponding to low flash potential.
(23) VF weighted Flash map-Inner Bezel Region-Normalized area corresponding to low flash potential.
(24) VF weighted Flash map-Outer Bezel Region-Normalized area corresponding to low flash potential.

As previously described herein, the size of the virtual facets (VF) may be factored in the flash and fire maps to create VF weighted Flash and Fire scintillation potential maps as shown in FIG. 4A-4G. Because the size of the virtual facets correspond to the size of "sparkles" in a scintillating diamond, these maps can be useful for grading purposes and for displaying the areas of the stone where the large flash or fire sparkles are expected to be observed. Larger sparkles (areas) are generally preferred in a gemstone as they are more visible to the human eye and, therefore, a gemstone with a smaller number of larger sparkles will generally have more visible scintillation than a stone with a larger number of smaller sparkles even if they have the same resultant sparkling area and light return. The size of the virtual facets can be computed as either an absolute size in square millimeters or as a relative size, expressed as a percentage of the total area of the stone.

The value of the VF weighted maps is that when the coded flash potential of the gemstone is weighted according to the virtual facet size for each orientation of the gemstone during the creation of the cumulative maps, the visibility of the potential is taken into account. Such a weighting favors gemstones where the average VF size stays larger when the gemstone is tilted and is therefore useful for many grading and comparison purposes when such discrimination is desirable. Essentially, such a weighting can better predict how visible the scintillation is to a human observer, vs. to a computer calculation. Cumulative maps may also include "weighted averages" where the map is scaled with regards to the angle of tilt. For example, a face-up flash counts more than that occurring at a 45 degree tilt as an observer is more likely to view the gemstone face-up or close to face-up and therefore is more likely to see a flash occur at this orientation. In an extreme example, a user would generally be completely unable to see a flash present from viewing the gemstone from under the table, as the gemstone's mount is likely blocking the view of the gemstone from that position. Thus, flash potential from such an observation point is essentially valueless (other than it may tell a jeweler to mount the gemstone in a different orientation).

In another scheme for scintillation quantification, the "speed" of flash changes can be measured in order to generate dynamic scintillation maps and corresponding data. Such a map would show areas where there is more change occurring. As a scintillation is effectively a flash effect, an area where path changes occurred multiple times through the same rotation as an area where only a single path change occurred may produce more scintillation. They can potentially flash multiple times when the gemstone is rotated or may provide flash to multiple different observation points. As discussed above, the speed of change can be obtained through the intelligent analysis as this necessarily takes into account the number of path changes (virtual facet edges and on/off events) for each point in a given rotation.

The coding of a dynamic scintillation map (not shown) would generally correspond to the "speed" flashes turn on/off (the number of path changes or edges) when the stone is in movement. In an embodiment, the speed can be based on a single observation (or source) point. Such a map would effectively "count" the number of flashes seen through the rotation from that observation point or with a light source at that point. Alternatively, the sheer number of path changes may be counted. As a diamond moves through different orientations, each point on the crown draws light from different directions of the panorama. The "rate of change" of these direction changes correspond to the speed of flash changes.

In an embodiment, the following method may be used to generate dynamic scintillation maps. A 3-D model of a diamond is moved through a fine grained pattern of orientations, approximating the set of all possible orientations within a specified angular range, say 0 to x degrees of tilt, in y degree increments, and 0 to 360 degree on azimuth in z degree increments. Consider a single point P on the crown of the diamond and a sphere S of radius r, surrounding the diamond. For each orientation of the diamond, T(o,P) corresponds to the point s on S, where P draws light when the stone is in orientation o. This is computed by reverse ray tracing the diamond from the eye through point P as discussed previously. As the number of orientations approaches infinity, the set of all points s corresponding to T(o,P) form "blobs" on the sphere S. The total area, quantity, and distribution of these blobs around S is related to the speed of scintillation and can be used to color code a map and estimate the rate of change. In general, larger total areas (more spread coordinates x,y,z) correspond to longer/faster scans of the panorama and therefore faster flash scintillation. Further, more changes in path during this tilt also correspond to increased scintillation as light is being taken in form different point sources. Conversely small, more localized blobs (densely packed coordinates x, y, z) and/or fewer path changes mean that P draws light from near the same area from the environment in all orientations, therefore the flashes near P tend to be slower and less dynamic as under real illumination conditions there is less chance to draw light from a different area.

Dynamic scintillation maps effectively add to the comparison that the source of light in a real-world environment is likely not consistent as the light supplied to the gemstone is not a series of point sources, but a continuous spectrum. Thus, as a gemstone moves, the more disparate the sources of light are which are being directed through any particular point to the observer, the more likely that the observer will see a visible change. Thus, while the flash and fire potential maps provide for indications where scintillation effects are more likely to be seen generally (because there is light being seen), the dynamic map provides for an indication of the likelihood of changes to occur. Combined together, an area with high light return (flash) and high dynamic change (movement) is likely to create an area of very visible scintillation.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method to display the scintillation of a gemstone, the method comprising:
   acquiring the angular spectrum of art oriented gemstone relative a point of observation by:
   tracing a ray to said gemstone from said, point of observation to a point of intersection of said gemstone;
   propagating said ray in said gemstone until it exits said gemstone;
   determining a region of a hemisphere arranged about said gemstone that said ray intersects;
   coding said point of intersection with a value according to said region that said ray intersects;
   repeating said steps of tracing, propagating, determining and coding for a plurality of points of intersection of said gemstone;
   tilting said gemstone to a new orientation relative to said point of observation and repeating said acquiring for said gemstone in said new orientation relative to said point of observation, said point of intersection and said plurality of points of intersection in said repeating being the same point of intersection and plurality of points of intersection as in said acquiring;
   repeating said tilting a pre-determined number of times;
   for each point of intersection, averaging said values for said eta point of intersection from all said acquiring;
   for each point of intersection, mapping said average value of said point of intersection to a location on an image of said gemstone, said location corresponding to said point of intersection on said gemstone.

2. The method of claim 1 wherein said gemstone is a diamond.

3. The method of claim 1 wherein said rays correspond to white light and said mapping displays flash scintillation potential.

4. The method of claim 1 wherein said rays correspond to colored light and said mapping displays fire scintillation potential.

5. The method of claim 1 wherein said mapping includes virtual facets.

6. The method of claim 1 wherein said mapping comprises color-coding.

7. The method of claim 1 wherein said mapping comprises shading.

8. A scintillation potential map produced by the method of claim 1.

9. A computer system for evaluating gemstone, the system comprising:
   means for acquiring the angular spectrum of an oriented gemstone relative a point of observation by:
   tracing a ray to a computer readable representation of said gemstone from said point of observation to a point of intersection of said gemstone;
   propagating said ray in said gemstone until it exits said gemstone;
   determining a region of a hemisphere arranged about said gemstone that said ray intersects;
   coding said point of intersection with a value according to said region that said ray intersects; and
   repeating said steps of tracing, propagating, determining and coding for a plurality of points of intersection of said gemstone;
   means for tilting said computer readable representation of said gemstone to a new orientation relative to said point of observation and repeating said acquiring for said computer readable representation of said gemstone in said new orientation relative to said point of observation, said point of intersection and said plurality of points of intersection in said repeating being the same point of intersection and plurality of points of intersection as in said acquiring;
   means for repeating said tilting a pre-determined number of times;
   means for, for each point of intersection, averaging said values for said each point of intersection from all said acquiring; and
   means for, for each point of intersection, mapping said average value of said point of intersection to a location on an image of said gemstone, said location corresponding to said point of intersection on said gemstone.

10. A non-transitory computer readable medium comprising:
    computer readable instructions for acquiring the angular spectrum of an oriented gemstone relative a point of observation by:
    tracing a ray to a computer readable representation of said gemstone from said point of observation to a point of intersection of said gemstone;
    propagating said ray in said gemstone until it exits said gemstone;

determining a region of a hemisphere arranged about said gemstone that said ray intersects;

coding said point of intersection with a value according to said region that said ray intersects; and repeating said steps of tracing, propagating, determining and coding for a plurality of points of intersection of said gemstone;

computer readable instructions for tilting said computer readable representation of said gemstone to a new orientation relative to said point of observation and repeating said acquiring for said computer readable representation of said gemstone in said new orientation relative to said point of observation, point of intersection and said plurality of points of intersection in said repeating being the same point of intersection and plurality of points of intersection as in said acquiring;

computer readable instructions for repeating said tilting a pre-determined number of times;

computer readable instructions for, for each point of intersection, averaging said values for said each point of intersection from all said acquiring; and computer readable instructions for, for each point of intersection, mapping said average value of said point of intersection to a location on an image of said gemstone, said location corresponding to said point of intersection on said gemstone.

\* \* \* \* \*